United States Patent
McKnight et al.

(10) Patent No.: US 6,812,697 B2
(45) Date of Patent: Nov. 2, 2004

(54) MOLDED EDDY CURRENT ARRAY PROBE

(75) Inventors: William Stewart McKnight, Hamilton, OH (US); Shridhar Champaknath Nath, Niskayuna, NY (US); Sandie Elizabeth Gresham, Cincinnati, OH (US); Richard Lloyd Trantow, Depoe Bay, OR (US); Douglas Edward Ingram, Cincinnati, OH (US); John William Ertel, New Vienna, OH (US); Thomas James Batzinger, Burnt Hills, NY (US); Curtis Wayne Rose, Mechanicville, NY (US); Francis Howard Little, Cincinnati, OH (US)

(73) Assignee: General Electric Company, Schenectady, NY (US)

(*) Notice: Subject to any disclaimer, the term of this patent is extended or adjusted under 35 U.S.C. 154(b) by 0 days.

(21) Appl. No.: 10/253,848

(22) Filed: Sep. 24, 2002

(65) Prior Publication Data

US 2004/0056656 A1 Mar. 25, 2004

(51) Int. Cl.$^7$ ............................................. G01N 27/90
(52) U.S. Cl. ....................................... 324/262; 324/242
(58) Field of Search ........................ 73/866.5; 324/262, 324/242, 219–221, 238, 234; 336/212; 264/272.19; 29/606

(56) References Cited

U.S. PATENT DOCUMENTS

| | | | |
|---|---|---|---|
| 5,136,240 A | 8/1992 | Geier et al. | |
| 5,315,234 A | 5/1994 | Sutton, Jr. et al. | |
| 5,442,286 A | 8/1995 | Sutton, Jr. et al. | |
| 5,841,277 A | 11/1998 | Hedengren et al. | |
| 5,903,147 A | 5/1999 | Granger, Jr. et al. | |
| 6,029,530 A | 2/2000 | Patton et al. | |
| 6,198,280 B1 | 3/2001 | Hensley et al. | |
| 6,469,503 B2 * | 10/2002 | Trantow et al. | ............. 324/219 |

OTHER PUBLICATIONS

Pending patent application Ser. No. 09/697,256, filed Oct. 27, 2000.

* cited by examiner

*Primary Examiner*—Jay Patidar
*Assistant Examiner*—Reena Aurora
(74) *Attorney, Agent, or Firm*—William Scott Andes; Armstrong Teasdale LLP

(57) ABSTRACT

The present invention provides an eddy current array probe having a complaint body molded around a rigid insert. A flexible eddy current array circuit is wrapped around the outer surface of the compliant body.

12 Claims, 6 Drawing Sheets

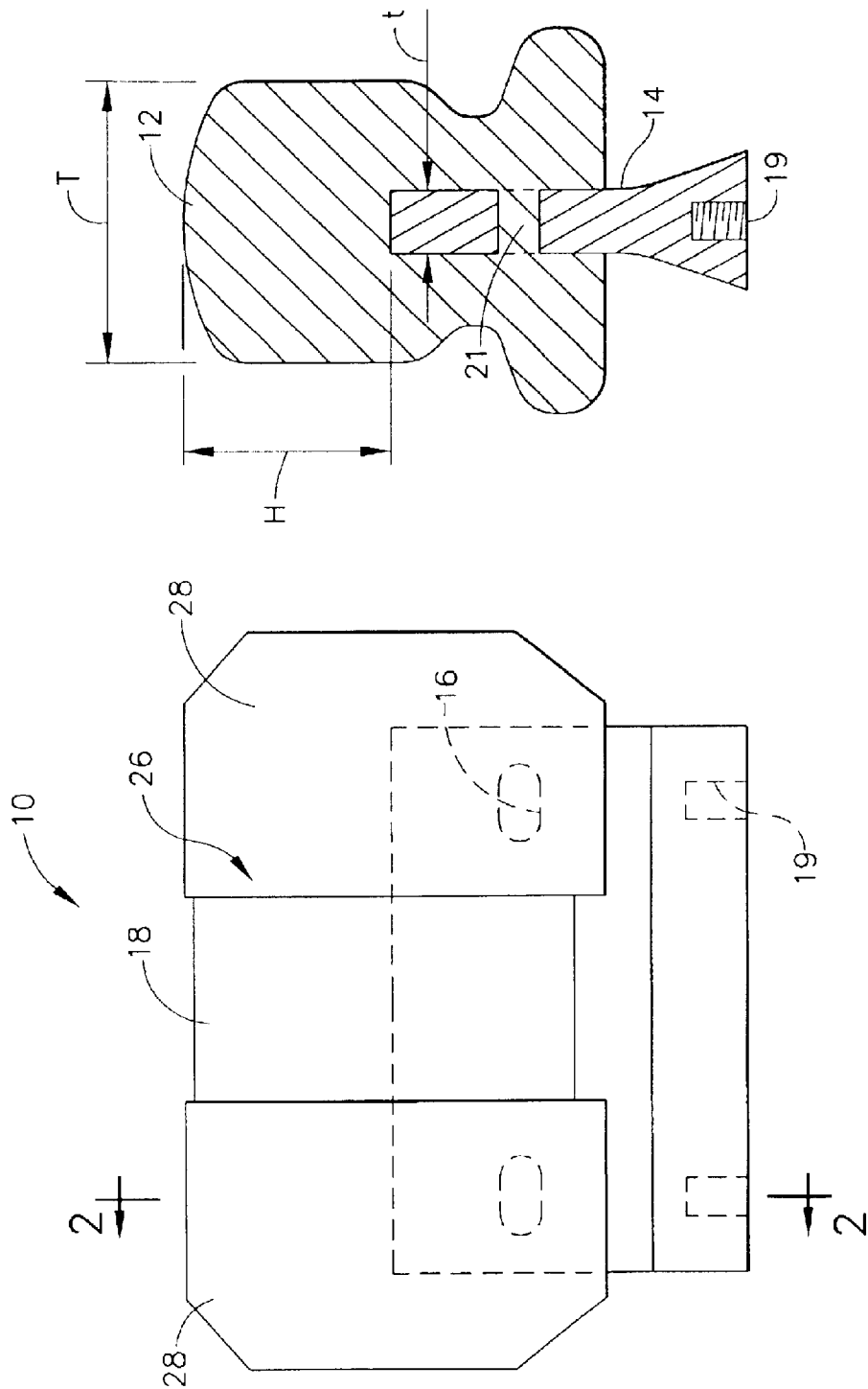

MOLDED EDDY CURRENT ARRAY PROBE

BACKGROUND OF THE INVENTION

The present invention relates to the inspection of components using eddy current technology and, more particularly, to a device for inspecting a component having a complex geometric shape, such as a dovetail slot, gear tooth or the like of a gas turbine engine component or similar workpiece using a multiplicity of eddy current probe or circuit elements formed in an array.

Eddy current inspection is a commonly used technique for detecting discontinuities or flaws in the surface of components such as the components of a gas turbine engine. Eddy current techniques are based on the principle of electromagnetic induction in which eddy currents are induced within the component under inspection. The eddy currents are induced in the component by alternating magnetic fields created in a coil of an eddy current probe, referred to as a drive coil, when the probe is moved into proximity with the component under inspection. Changes in the flow of eddy currents are caused by the presence of a discontinuity or a crack in the test specimen. The altered eddy currents produce a secondary magnetic field which is received by the eddy current probe coil or by a separate sense coil in the eddy current probe which converts the altered secondary magnetic field to an electrical signal which may be recorded for analysis. An eddy current machine operator may then detect and size flaws by monitoring and analyzing the recorded signals.

One problem with inspecting the surface of a workpiece with an eddy current array is to maintain the array in conformance and/or contact with the surface, as the eddy current device or probe is scanned across the surface, and to cause each of the pluralities of drive and sense elements comprising the eddy current array to be maintained at their respective substantially constant distances from the inspection surface during scanning. Additionally, workpiece geometries may vary from one component to another because of manufacturing process variability. Variation in the distance between the drive and sense elements and the inspection surface or a gap between the probe and the inspection surface as the probe is scanned across the surface is referred to as liftoff and is undesirable.

Previous attempts have been made to create probes that are flexible enough to conform to the surface being inspected, for example by placing an eddy current probe having a soft rubber backing, a corrugated cover, and an eddy current array over an expandable bar device. A pneumatically-powered wedge apparatus is then used to force the eddy current array into intimate contact with the surface being inspected. Unfortunately, this probe construction is less than ideal and requires increased pneumatic pressure in order to force the probe to conform with the surface being inspected, which tends to wear out the probe rapidly.

Accordingly, there is a need for an eddy current array probe that can maintain an eddy current array in contact with a part feature without the application of excessive force.

BRIEF SUMMARY OF THE INVENTION

The above-mentioned need is met by the present invention, which provides an eddy current array probe having a complaint body molded around a rigid insert. A flexible eddy current array circuit is wrapped around the outer surface of the compliant body.

The present invention and its advantages over the prior art will become apparent upon reading the following detailed description and the appended claims with reference to the accompanying drawings.

BRIEF DESCRIPTION OF THE DRAWINGS

The subject matter that is regarded as the invention is particularly pointed out and distinctly claimed in the concluding part of the specification. The invention, however, may be best understood by reference to the following description taken in conjunction with the accompanying drawing figures in which:

FIG. 1 is a side view of an eddy current array probe constructed in accordance with the present invention.

FIG. 2 is cross-sectional view of the eddy current array probe of FIG. 1.

DETAILED DESCRIPTION OF THE INVENTION

Figure 3:
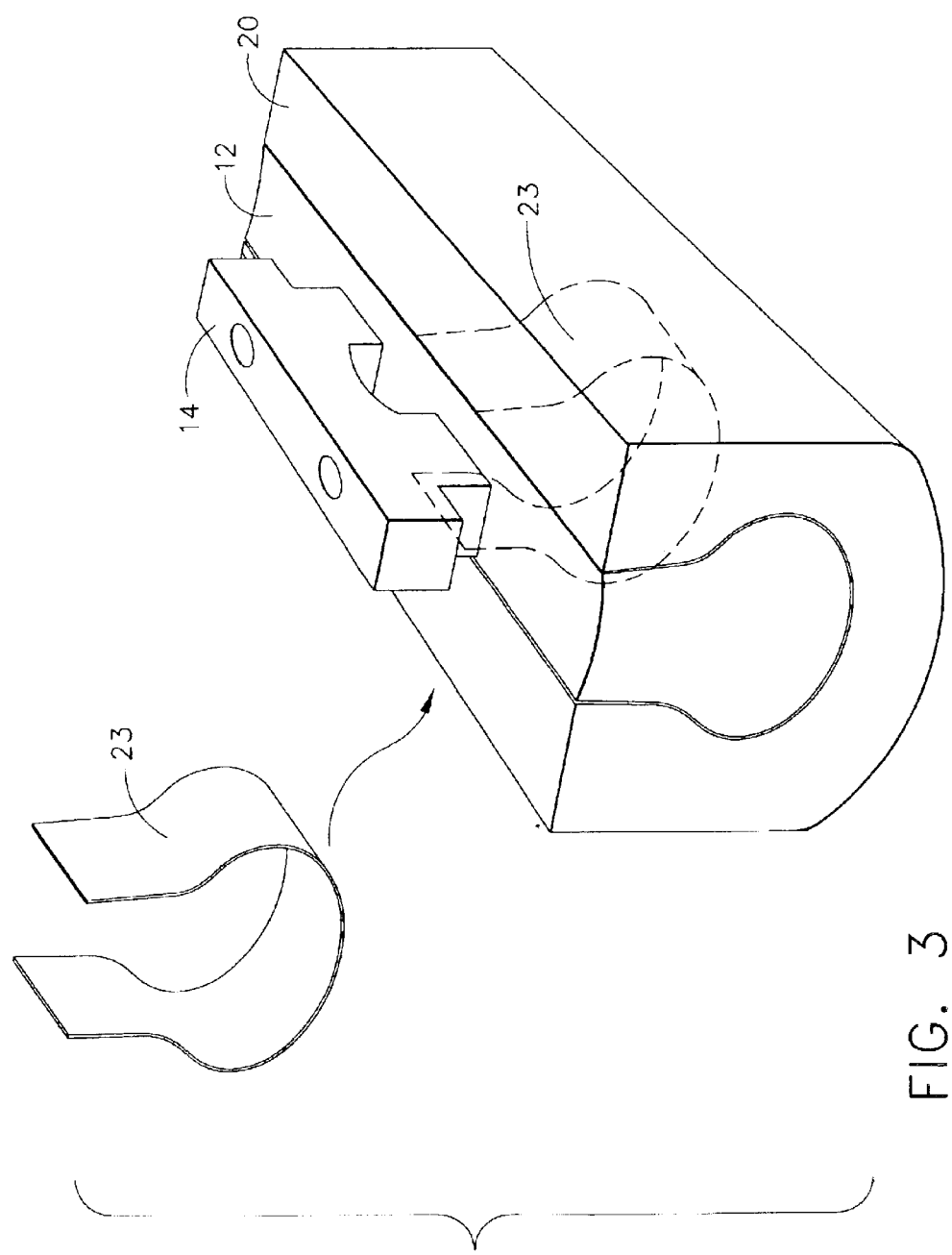
FIG. 3 is a schematic perspective view of a mold for the eddy current probe of the present invention.

Referring to the drawings wherein identical reference numerals denote the same elements throughout the various views, FIGS. 1 and 2 illustrate an exemplary eddy current probe 10. The probe is comprised of two major components, a compliant probe body 12 and relatively rigid insert 14. The probe body 12 is an elongated shape corresponding to the surface to be inspected and is cast from a liquid compound that forms a flexible material when cured, which is discussed in more detail below. The probe body 12 is adhered to the insert 14. The insert 14 is fabricated, for example molded or machined, from a relatively rigid material. Any relatively rigid, preferably non-conducting material that may be bonded to the compliant probe body during the casting process, and that is dimensionally stable over time, may be used, including such materials as metal, wood, LEXAN polycarbonate, or PLEXIGLAS acrylic resin. One suitable material for the insert 14 is DELRIN acetal resin, available from E.I. DuPont de Nemours and Company, Wilmington, Del. 19898. A castable relatively rigid polyurethane may also be used. The insert 14 incorporates attachment features 19 for attaching the insert 14 to a structure used to support and manipulate the probe 10. In the example shown the attachment features 19 take the form of internally threaded holes for receiving threaded fasteners (not shown). The threaded fasteners may be screwed into the base of the insert 14, bonded into holes in the base of the insert 14, or cast into the insert 14 if the insert is formed by a casting process. The insert 14 may also have one or more slots 16 extending through its thickness. During the casting process, as described below, a portion of the flexible material which forms the probe body 12 flows into the slots 16 of the insert 14, forming one or more integral anchors 21 when the flexible material has cured. The integral anchors 21 may have a shape similar to cylindrical pins. The integral anchors 21 help to retain the insert 14 in the probe body 12.

The probe 10 is manufactured by casting a fluid compound that cures to form a flexible material around the insert 14. Initially a mold 20 (see FIG. 3) is provided. The mold 20 has an internal cavity which duplicates the shape and dimensions of the actual part to be inspected. By way of example only, the part to be inspected is a rotor disk dovetail post. However, the present invention may be used with other components as well. An eddy current inspection standard for the part to be inspected may be used for the mold. Alternatively, a mold may be fabricated by making a negative mold of the inspection standard or the actual part to be inspected, and then using the negative to make a positive mold. Or, a mold may be made by providing a rough blank, and machining the desired features, for example by electro-discharge machining (EDM). Once the mold 20 is provided, the insert 14 is positioned in the proper relationship to the mold 20. A flexible material which is fluid in the uncured state is then poured around the insert 14 and allowed to cure. The flexible material used should have the proper flexibility and preferably also have the ability to self-bond to the insert 14. Depending on the flexible material used the probe body 12 may not self-bond to the insert 14, in which case the integral anchors 21 serve to retain the flexible material to the insert. One example of a suitable flexible material is TC 5050 RTV compound, available from BJB Enterprises, Inc., 14791 Franklin Avenue, Tustin, Calif. 92780, having a cured durometer hardness of about 20A to about 80A. The flexible material bonds to the insert 14, and as mentioned previously, a portion of the flexible material flows into the slots 16 of the insert 14, forming one or more pins 21 integral to the probe body 12 when the flexible material has cured, which help to retain the insert 14 in the probe body 12.

At the time of molding, a recess 18 extending around the outer surface of the probe body 12 may be formed in the probe body 12 in order to receive a portion of an eddy current array circuit 22, as discussed in more detail with reference to FIG. 4. The recess 18 may be formed by placing a strip of tape 23 of suitable thickness into the mold 20 in order to displace a portion of the flexible material. FIG. 3 illustrates the strip of tape 23 and also its position when placed in the mold 20, as shown by dashed lines. The recess 18 locates the eddy current array circuit 22 with respect to the long direction of the probe body 12 and also partially reduces the protrusion of the eddy current array circuit 22 from the surface of the probe body 12 when the probe 10 is assembled. The depth of the recess 18 should be substantially equal to the thickness of the eddy current array circuit 22 plus the thickness of any tape or glue layer that may be used to bond the eddy current array circuit 22 to the probe body 12, but should not be any deeper. It is also possible to use the invention without a recess 18 by accepting more compression of the probe body 12 during an inspection.

After the liquid rubber has cured, the probe 10 is removed from the mold 20. The probe body 12 is then trimmed to its final dimensions. The finished probe body 12 has a center section 26 that is left as-cast and is the full dimension of the part feature to be inspected (excepting the recess 18 if incorporated), and one or more tapered sections 28 located at opposite ends of the probe body 12 which are of a reduced dimension in order to ease insertion of the probe body 12 into the part feature to be inspected. These tapered sections 28 may also be cast into the probe body 12 either by adding material to the ends of the mold or by creating a 3-part mold with tapered end pieces.

The compliant nature of the probe body 12 is a result of the combination of the hardness of the flexible material chosen and the dimensions of the probe body 12. The flexible material must be soft enough to allow compliance of the probe body 12 to the part features and hard enough to create pressure to force the eddy current array circuit 22 into conformance with the part features. The amount of compliance is related to the relative dimensions of the probe body 12 and the insert 14 as well as the actual hardness of the material. For example, if the insert is too large relative to the probe body, only a small thickness of the probe body material would be available to compress and would likely be too stiff to conform properly. On the other hand, if the probe body 12 is too thick it would not be stiff enough to provide the proper pressure against the part feature alone and would require a relatively larger insert, or a harder material. In the illustrated example, the lateral thickness T of the probe body 12 (see FIG. 2) is approximately 19 mm (0.75 in.), which is approximately 3.75 times the thickness t of the insert 14, and the height H of the probe body 12 above the end of the insert 14 is approximately 14 mm (0.55 in.).

Figure 4:
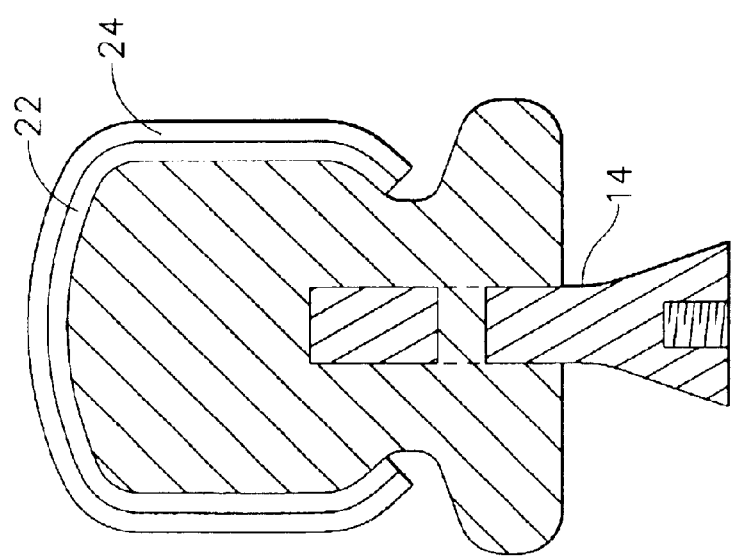
FIG. 4 is a cross-sectional view of an eddy current probe constructed in accordance with the present invention.

Referring now to FIG. 4, a flexible eddy current array circuit 22 is wrapped around the probe body 12. If a recess 18 is incorporated into the probe body 12, the eddy current array circuit 22 is seated into the recess 18. The eddy current array circuit 22 may be attached to the probe body 12, for example with an adhesive in the form of a tape or glue layer. The eddy current array circuit 22 and the probe body are then covered with a protective cover 24. The cover 24 protects the eddy current array circuit 22 from abrasion and allows the probe 10 to slide into a part feature more easily. The cover 24 may be formed from an adhesive-backed tape, for example a tape made of polytetrafluoroethylene (PTFE) resin, KAPTON polyimide film, or a similar material. The cover 24 adheres to the probe body 12 and retains the eddy current array circuit 22 in position.

Figure 5:
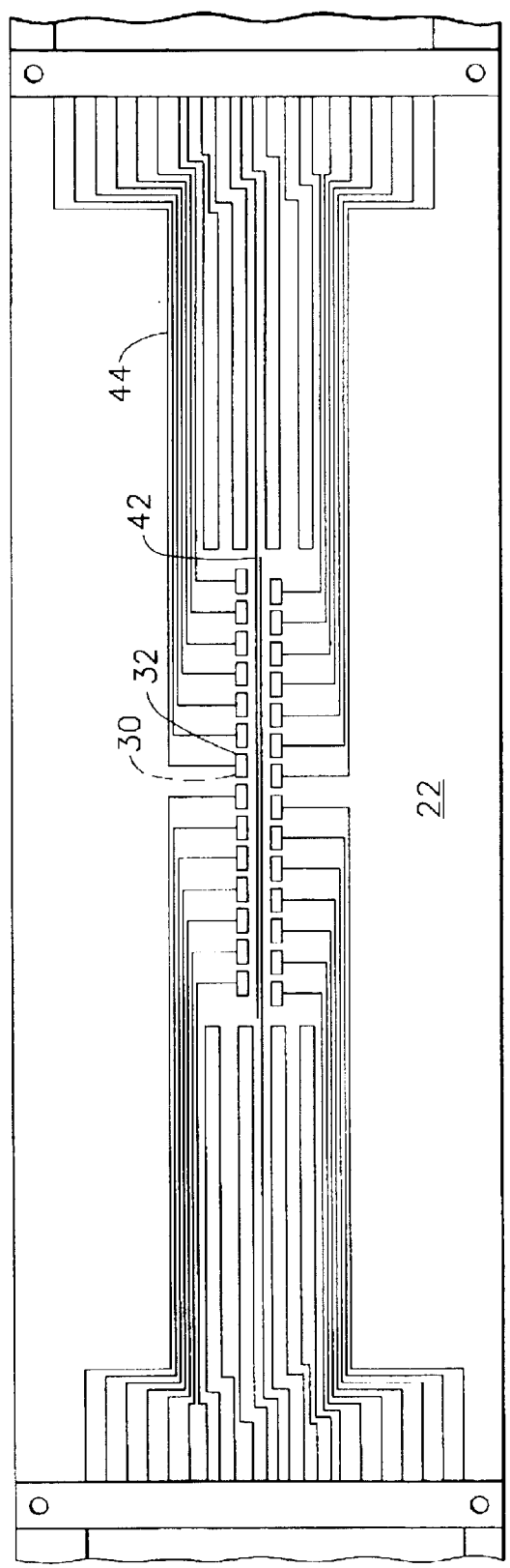
FIG. 5 is a schematic view of a flexible eddy current array circuit suitable for use with the eddy current array probe of the present invention.
Figure 6:
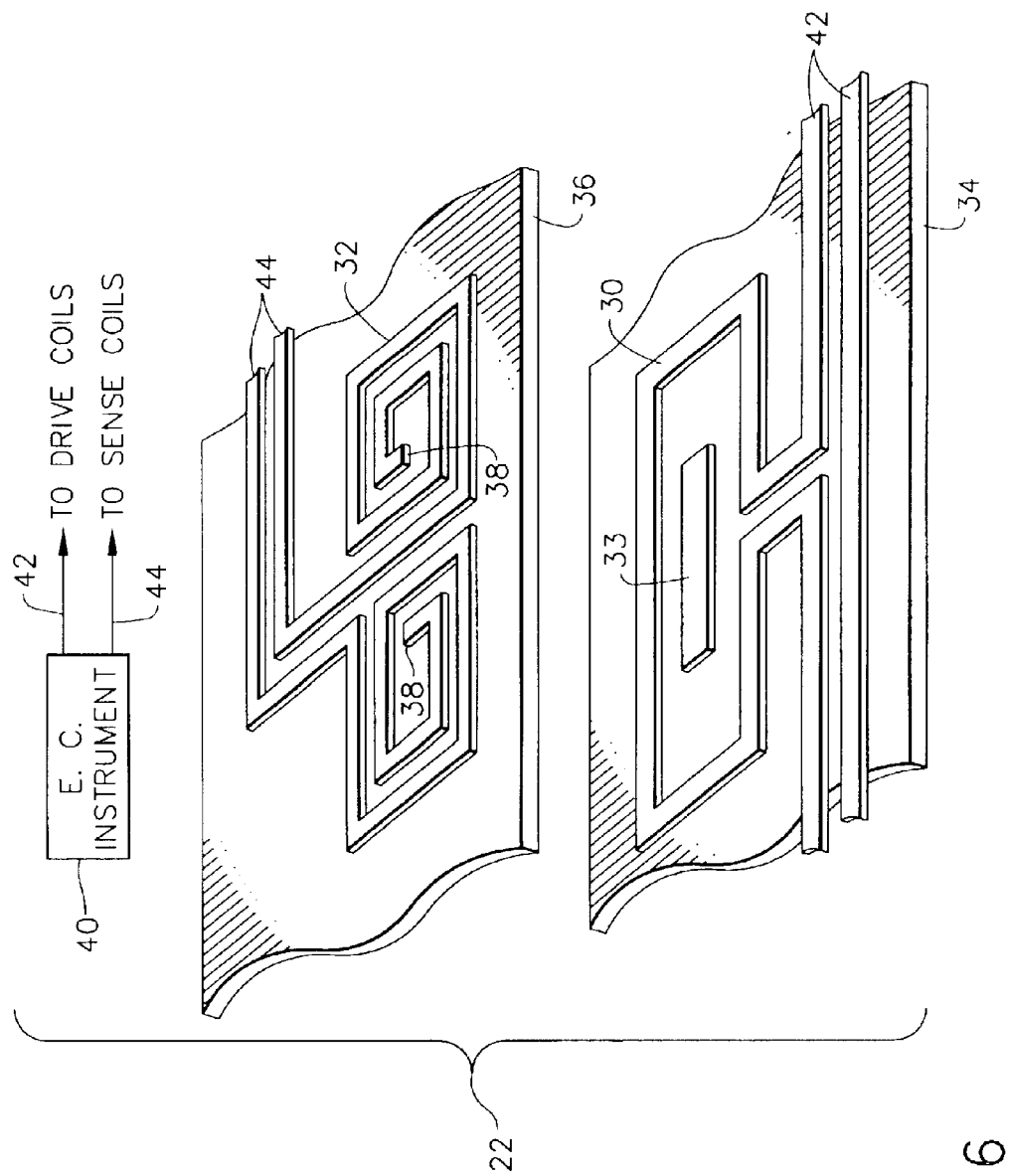
FIG. 6 is a perspective view of the flexible eddy current array circuit of FIG. 5.

An example of an eddy current array circuit 22 which may be used with the eddy current array probe 10 of the present invention is shown schematically in FIG. 5. The circuit 22 includes a plurality of drive coils 30 and sense coils 32 which may be disposed one above the other in different flexible layers or substrates 34 and 36 as best shown in FIG. 6. The substrates 34 and 36 may be formed from a material such as a KAPTON polyimide film and have a typical thickness of about 25 $\mu$m. The substrates 34 and 36 are shown separated in an exploded perspective view in FIG. 6 for purposes of clarity and explanation. Holes or vias 38 are formed through the substrate 36 for electrically interconnecting the sense coils 32 by a shorting strip 33 disposed on the other substrate 34. Those skilled in the art will recognize that the coils 30 and 32 could also be configured to reside in the same layer or substrate. Electrical contact is made between drive coils 30 and an eddy current instrument 40 (shown schematically in FIG. 6) by conductors 42 and electrical contact is made between the sense coils 32 and the eddy current instrument 40 by conductors 44. As shown in FIG. 5, both conductors 42 and 44 are brought out to the respective outer edges of the substrates 34 and 36 of the eddy current array circuit 22 to provide means for connecting the flexible eddy current array circuit 22 to the eddy current instrument 40. Other types of flexible eddy current array circuits could be used as well with the present invention, for example an L-shaped circuit having drive and sense coils at one end and electrical connections at the opposite end.

Figure 8:
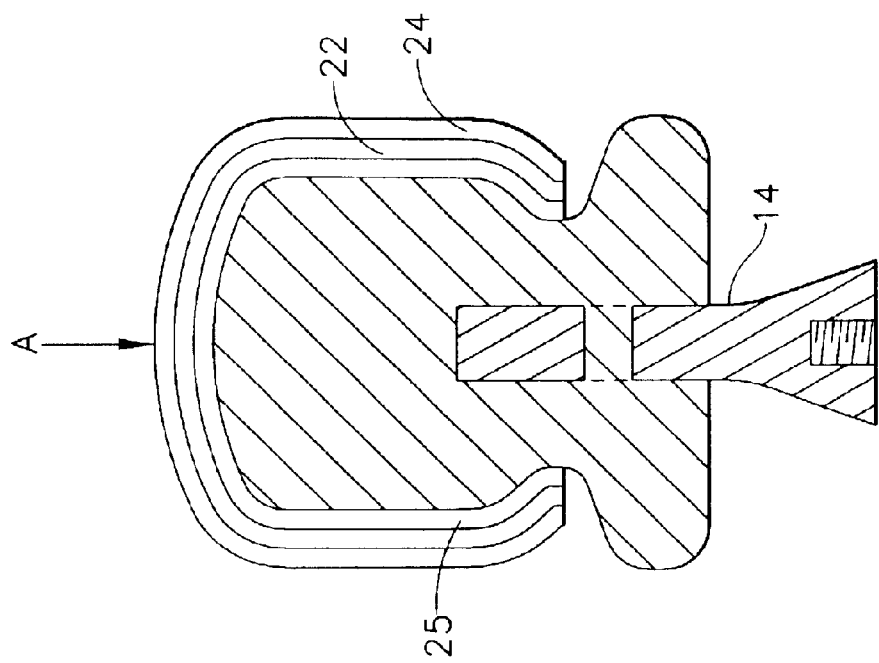
FIG. 8 is a cross-sectional view of an alternate arrangement of an eddy current probe constructed in accordance with the present invention.

Optionally, an underlayer 25 of a relatively slippery or self-lubricating material such as a polytetrafluoroethylene (PTFE) film may be used between the probe body 12 and the flexible eddy current array circuit 22, as illustrated in FIG. 8. Furthermore, the circuit 22 may be bonded to the probe body 12 at a single circumferential location as shown by the arrow labeled A in FIG. 8, for example by a line or narrow strip of an adhesive material, while the remainder of the circuit 22 is left unbonded. Either of these arrangements may help to eliminate any potential buckling and consequent lift-off of the circuit 22 during an inspection by allowing the relatively incompressible circuit 22 (or a portion thereof to slide circumferentially with respect to the probe body 12 as the probe 10 is inserted into a part feature.

Figure 7:
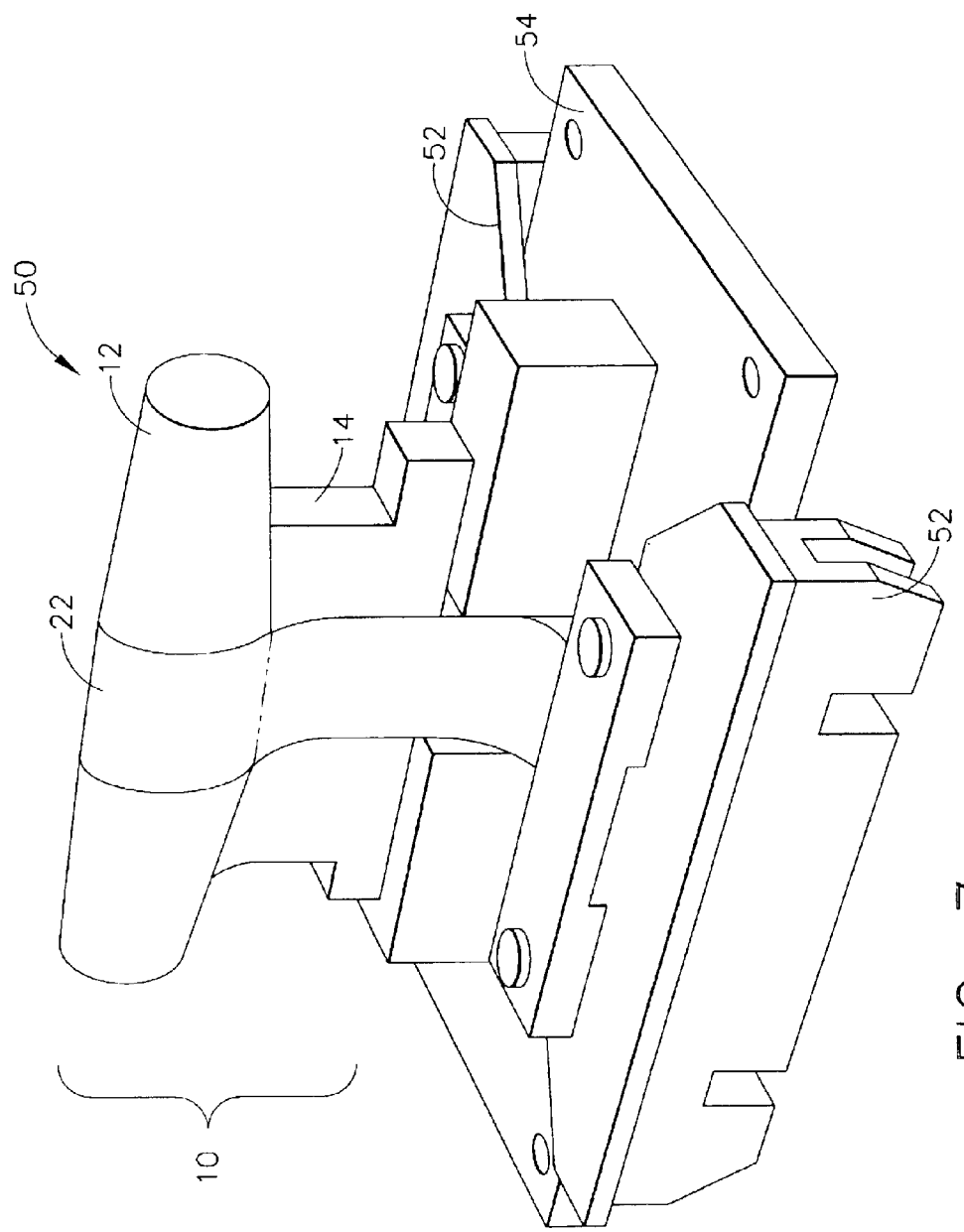
FIG. 7 is a perspective view of an eddy current probe assembly incorporating the eddy current probe of the present invention.

FIG. 7 illustrates an exemplary probe assembly 50 incorporating the eddy current probe 10 of the present invention. The eddy current probe 10 as described above, including the probe body 12, insert 14, eddy current array circuit 22, and protective cover 24, is attached to a base plate 54, for example with threaded fasteners (not shown). The base plate 54 provides a means by which the eddy current probe 10 can be attached to a structure for supporting and manipulating the eddy current sensor 10. One or more electrical connectors 52 are also attached to the base plate 54. The leads 42, 44 of the eddy current array circuit are electrically connected to terminals within the electrical connectors 52. The probe assembly 50 thus provides a convenient way to make the necessary mechanical and electrical connections to the eddy current probe 10.

In operation, the eddy current probe 10 is connected to an eddy current instrument 40. The eddy current probe 10 is then traversed along the part feature to be inspected. As previously explained, the probe body 12 is the same dimensions as the part feature to be inspected. When the eddy current array circuit 22 and the protective cover 24 are added to the probe body 12, the overall probe dimensions become slightly larger than the part feature. This results in a slight compression of the probe body 12 and a predictable force urging the eddy current array circuit 22 against the surface of the part feature.

The relative softness of the probe body 12 allows it to be flexible and provides the necessary compressional compliance and provides improved control over conformity with the surface of the part feature being inspected. The better the fit between the probe's surface and the feature to be inspected, the lower the probe expansion forces needed to force a fit with the surface, and the smaller the axial force required to pass the probe through the inspection area. These reductions in force translate into lower friction forces and therefore longer probe life. Additionally, production time and cost of the eddy current probes 10 is reduced considerably compared to prior art designs, because of the simple method of manufacture and small number of parts.

While the example disclosed herein is of a probe 10 intended to inspect dovetail slots in gas turbine engine disks, the probe structure of the present invention may be used for many different applications, including but not limited to air slot features, bolt holes, bore corners, rabbets, and web transition regions of rotating or non-rotating parts and other surfaces. The molding technique is equally applicable to array probe configurations for the inspection of other surface shapes, from flat surfaces to toroids.

The foregoing has described an eddy current array probe having a compliant body molded around a rigid insert. While specific embodiments of the present invention have been described, it will be apparent to those skilled in the art that various modifications thereto can be made without departing from the spirit and scope of the invention as defined in the appended claims.

What is claimed is:

1. An eddy current probe, comprising:

an insert comprising at least one slot;

a compliant probe body adhered to said insert and extending at least partially into said at least one slot, said probe body formed in the shape of a workpiece to be inspected; and a flexible eddy current array circuit disposed on said probe body.

2. The eddy current probe of claim 1 further comprising a protective cover disposed over said eddy current array circuit.

3. The eddy current array probe of claim 1 wherein said compliant probe body comprises a material softer than said insert.

4. The eddy current array probe of claim 1 wherein said compliant probe body comprises a recess for receiving said eddy current array circuit.

5. The eddy current array probe of claim 1 further comprising an underlayer disposed between said probe body and said eddy current array circuit.

6. The eddy current array probe of claim 1 wherein said eddy current array circuit is bonded to said probe body at a single circumferential location.

7. An eddy current probe, comprising:

an insert having at least one slot extending therethrough;

a compliant probe body disposed around said insert, said probe body having an external surface formed in the shape of a workpiece to be inspected and an internal surface formed in the shape of said insert, said probe body comprising at least one integral anchor extending through said slot; and a flexible eddy current array circuit disposed on said probe body.

8. The eddy current probe of claim 7 further comprising a protective cover disposed over said eddy current array circuit.

9. The eddy current array probe of claim 7 wherein said compliant probe body comprises a material softer than said insert.

10. The eddy current array probe of claim 7 wherein said compliant probe body comprises a recess for receiving said eddy current array circuit.

11. The eddy current array probe of claim 7 further comprising an underlayer disposed between said probe body and said eddy current array circuit.

12. The eddy current array probe of claim 7 wherein said eddy current array circuit is bonded to said probe body at a single circumferential location.

* * * * *